US011338219B2

(12) United States Patent
Noh (10) Patent No.: US 11,338,219 B2
(45) Date of Patent: May 24, 2022

(54) DIVIDING WALL DEBUTANIZER COLUMN, SYSTEM AND METHOD OF OPERATION

(71) Applicant: SAUDI ARABIAN OIL COMPANY, Dhahran (SA)

(72) Inventor: Hae Yong Noh, Yanbu (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 50 days.

(21) Appl. No.: 16/992,661

(22) Filed: Aug. 13, 2020

(65) Prior Publication Data

US 2022/0047964 A1 Feb. 17, 2022

(51) Int. Cl.
| | | |
|---|---|---|
| *B01D 3/14* | (2006.01) | |
| *C07C 7/04* | (2006.01) | |
| *C10G 7/00* | (2006.01) | |
| *C10L 1/06* | (2006.01) | |

(52) U.S. Cl.
CPC ............... *B01D 3/141* (2013.01); *C07C 7/04* (2013.01); *C10G 7/00* (2013.01); *C10L 1/06* (2013.01); *C10G 2300/1081* (2013.01); *C10G 2400/02* (2013.01); *C10L 2270/023* (2013.01); *C10L 2290/543* (2013.01)

(58) Field of Classification Search
CPC .. B01D 3/141; C07C 7/04; C10G 7/00; C10G 2300/1081; C10G 2400/02; C10L 1/06; C10L 2270/023; C10L 2290/543
USPC .......................................................... 203/91
See application file for complete search history.

(56) References Cited

U.S. PATENT DOCUMENTS

| | | | |
|---|---|---|---|
| 5,453,177 A | 9/1995 | Goebel et al. | |
| 6,291,734 B1 | 9/2001 | Stork | |
| 6,551,465 B1 | 4/2003 | Van Zile et al. | |
| 8,066,868 B1 | 11/2011 | Zimmermann | |

(Continued)

FOREIGN PATENT DOCUMENTS

| | | |
|---|---|---|
| CN | 207047164 U | 2/2018 |
| JP | 2006241076 A | 9/2006 |

(Continued)

OTHER PUBLICATIONS

Lestak, Frigyes and Cyril Collins, "Advanced Distillation Saves Energy & Capital", Chemical Engineering, Jul. 1997, pp. 72-76 (5 pages).

(Continued)

*Primary Examiner* — Brian A McCaig
(74) *Attorney, Agent, or Firm* — Osha Bergman Watanabe & Burton LLP (57) ABSTRACT

Embodiments disclosed relate to a debutanizer with a dividing wall. The configuration of the debutanizer includes having a feed section, a top section, a bottom section, and a draw-off section. The debutanizer produces a C4s product, a C5s product and a natural gasoline (NG) product from a C4+s feed. The dividing wall is configured such that an upper portion of the dividing wall is positioned off-set from a vertical centerline and a lower portion of the dividing wall is positioned along the vertical centerline of the debutanizer. A process of use of the debutanizer is also disclosed. A natural gas liquids (NGL) system that includes parallel debutanizers, each with a dividing wall, and a process of use of such system, is also disclosed.

9 Claims, 4 Drawing Sheets

(56) References Cited

U.S. PATENT DOCUMENTS

| | | |
|---|---|---|
| 2003/0116420 A1* | 6/2003 | Kaibel .................... B01D 3/14 203/1 |
| 2011/0108458 A1 | 5/2011 | Leonard et al. |
| 2012/0141333 A1 | 6/2012 | Ulas Acikgoz et al. |
| 2017/0342002 A1 | 11/2017 | Zavala et al. |
| 2018/0202713 A1 | 7/2018 | Pek et al. |
| 2018/0216011 A1 | 8/2018 | Phu |
| 2020/0001198 A1 | 1/2020 | Frey et al. |

FOREIGN PATENT DOCUMENTS

| | | |
|---|---|---|
| RU | 2143459 C1 | 12/1999 |
| WO | 2017075209 A1 | 5/2017 |

OTHER PUBLICATIONS

International Search Report issued in corresponding International Application No. PCT/US2020/050640, dated Apr. 9, 2021 (4 pages).
Written Opinion issued in corresponding International Application No. PCT/US2020/050640, dated Apr. 9, 2021 (8 pages).

\* cited by examiner

DIVIDING WALL DEBUTANIZER COLUMN, SYSTEM AND METHOD OF OPERATION

BACKGROUND

Natural gas liquids (NGLs) are a source of useful light (C2-C7) alkanes. The alkanes found as condensate in natural gas sources not only provide a feedstock for natural gasoline (NG) but also feedstock for cracking units to make hydrogen and olefins, for example, ethane to ethylene and hydrogen, propane to propylene and hydrogen, et cetera. Full utilization of NGLs expands the energy and chemical supply portfolio.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments that are disclosed relate to a debutanizer. The apparatus may include a debutanizer having a dividing wall configuration such that there is a feed section, a top section, a bottom section, and a draw-off section. The feed section may be configured to receive and to partially fractionate an introduced alkane C4+s stream. The top section may be configured to fractionate top product components from middle product components and to produce an alkane C4s product stream. The bottom section may be configured to fractionate bottom product components from middle product components and to produce a natural gasoline (NG) product stream. The draw-off section may be configured to fractionate middle product components from both top and bottom product components and to produce an alkane C5s product stream. The dividing wall may be configured such that an upper portion of the dividing wall is positioned off-set from a vertical centerline of the debutanizer. At the same time, a lower portion of the dividing wall may be configured such that it is positioned along the vertical centerline of the debutanizer.

In another aspect, embodiments that are disclosed relate to a process of operating a debutanizer. The method may include introducing an alkane C4+s stream into a feed section of a debutanizer with a dividing wall, where the debutanizer has a feed section, a top section, a bottom section, and a draw-off section as previously described. The method may include operating the debutanizer such that an alkane C4s product stream passes from a top section, an alkane C5s product stream passes from the draw-off section, and a natural gasoline (NG) product stream passes from the bottom section. In such embodiments, the NG product stream requires no further adjustment to Reid vapor pressure (RVP) before gasoline blending.

In yet another aspect, embodiments that are disclosed relate to a natural gas liquids (NGL) refinery including more than one debutanizer. The system may include a first debutanizer with a dividing wall having a feed section, a top section, a bottom section, and a draw-off section, each as previously described. The dividing wall is configured such that the upper portion of the dividing wall is positioned off-set from a vertical centerline of the first debutanizer and the lower portion of the dividing wall is positioned along the vertical centerline of the first debutanizer. The system may also include a second debutanizer similar to the first debutanizer. In such a system the first and the second debutanizers may be coupled in parallel with each other. The system may be configured to produce a first alkane C4+s stream and a second alkane C4+s stream from an introduced unrefined NGL stream and introduce the first alkane C4+s stream and the second alkane C4+s stream to the first debutanizer and the second debutanizer, respectively. The system may also be configured to produce a combined C4s product stream from a first C4s product stream and a second C4s product stream, a combined C5s product stream from a first C5s product stream and a second C5s product stream, and a combined NG product stream from a first NG product stream and a second NG product stream.

In yet another aspect, embodiments that are disclosed relate to a process of operating a natural gas liquids refinery. The process may include introducing an unrefined natural gas liquid (NGL) stream into a NGL refinery. The NGL refinery has a first debutanizer with a dividing wall and a second debutanizer with a dividing wall, as previously described. Both the first and the second debutanizers are coupled in parallel relative to one another, as previously described. The process may include operating the NGL refinery such that a portion of the unrefined NGL stream is converted into a first alkane C4+s stream and a second alkane C4+s stream, such that the first alkane C4+s stream is introduced into the first debutanizer, and such that the second alkane C4+s stream is introduced into the second debutanizer. The process may include operating the first debutanizer such that the first alkane C4+s stream fractionates into a first C4s product stream that passes from a top section, a first C5s product stream that passes from a draw-off section, and a first natural gasoline (NG) product stream that passes from a bottom section, and operating a second debutanizer in a similar manner as the first debutanizer. The process may include operating the NGL refiner such that a first C4s product stream and a second C4s product stream form a combined C4s product stream, a first C5s product stream and a second C5s product stream form a combined C4s product stream, and a first NG product stream and a second NG product stream form a combined NG product stream. The process may include passing from the NGL refinery the combined C4s product stream, the combined C5s product stream, and the combined NG product stream from the NGL refinery. The combined NG product stream requires no further adjustment to Reid vapor pressure before gasoline blending.

Other aspects and advantages of this disclosure will be apparent from the following description made with reference to the accompanying drawings and the appended claims.

BRIEF DESCRIPTION OF DRAWINGS

Certain embodiments of the disclosure will be described with reference to the accompanying drawings, where like reference numerals denote like elements. It should be understood, however, that the accompanying figures illustrate the various implementations described and are not meant to limit the scope of various technologies described.

FIGS. 2D-1-3 is an inset showing several generalized variations for configuration of the middle portion of the dividing wall within embodiment debutanizers.

In the figures, down are toward or at the bottom and up are toward or at the top of the figure. "Up" and "down" are generally oriented relative to a local vertical direction. However, "upstream" in the oil and gas industry may more generally refer to objects, units or processes taken before a particular unit or process. As well, "downstream" may more generally refer to objects, units or processes taken after a particular unit or process.

DETAILED DESCRIPTION

Traditional natural gas liquids (NGL) refineries have issues in handling large volumes of butanes present in partially-refined NGLs while attempting to recover a useful natural gasoline (NG) fraction. Often, such units require the presence of a second column downstream of a debutanizer to assist in regulating Reid vapor pressure (RVP) of the natural gasoline fraction by pulling out excess pentanes. Such a two-column system not only requires additional units but also the heating and cooling systems to support both units, which is not efficient.

The purpose of the debutanizer with a dividing wall in a NGL refinery is to separate an incoming mixed stream of depropanized alkanes into three compositions: a refined butanes stream, an alkane C5s product stream with a relatively high isopentene concentration, and a natural gasoline (NG) stream that meets Reid vapor pressure (RVP) requirements for gasoline blending. The three product streams are produced from a single distillation column. This provides for reduced number of distillation columns downstream to further separate product streams.

With fewer columns in a train of processing units, a benefit is received by using less energy. Distillation is an energy-intensive activity, where fluids are heated, boiled, pumped, and condensed. In a train of units, the same composition may be heated or cooled several times before produced as a product. In a divided wall column, that energy is used in a single column to separate multiple components. Energy that would have been used in a greater number of columns to condense a material in one column and then heat the same material in another are saved.

In reducing the number of columns in a processing train, there are also fewer overall items to maintain. With the reduction in the number of units, there are also less auxiliary and ancillary systems, like pumps, compressors, heat exchangers, condensers, and sensors.

In counting the number of trays in a column, traditionally the count would start from the bottom upwards (for example, 1, 2, 3, et cetera).

Apparatus

Figure 1:
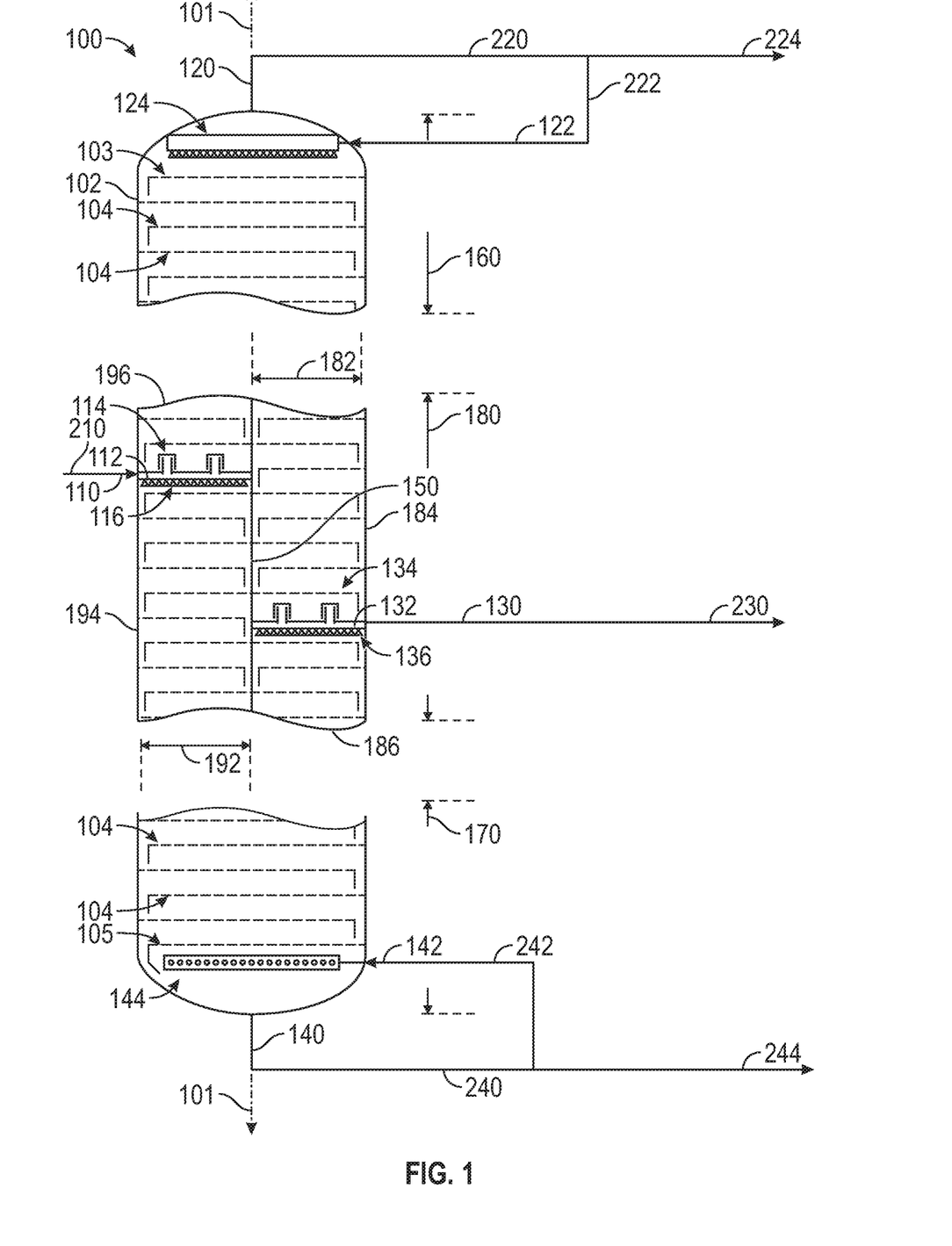
FIG. 1 shows a schematic of an embodiment dividing wall debutanizer column.

FIG. 1 shows a schematic of an embodiment dividing wall debutanizer column 100 ("debutanizer 100"). Debutanizer 100 has several inlet and outlet ports traversing shell 102 for fluid introduction and passing, including side inlet 110, overhead outlet 120, overhead return inlet 122, side outlet 130, bottoms outlet 140, and bottoms return inlet 142.

FIG. 1 also shows a dividing wall 150 bifurcating a portion of the debutanizer 100, making debutanizer 100 a dividing wall column. A dividing wall column is a fractional distillation column with a substantially fluid tight vertical wall extending through a significant portion of its height. Components of the feed as introduced can traverse the column upward and leave the column via the overhead product stream, can traverse the column either upward or downward and then pass from the column via the side draw, or can traverse the column downward and leave the column via the bottoms product stream. The separations performed in a dividing wall column are those normally performed in a conventional column.

The vertical wall is positioned in a middle portion or section (as viewed from bottom to top) of the column to divide this middle section into at least two vertical, parallel vapor-liquid contacting sections. The top and bottom of the dividing wall terminate in the column at a point distant from the respective ends of the column. There is open communication across the column interior at the top section of the column above the dividing wall. There is also open communication across the column interior at the bottom section of the column below the dividing wall for the entire diameter of the column. That is, vapor leaving the top of each of the partitioned middle sections and liquid leaving the bottom of each of the partitioned middle sections flow into common sections (top or bottom), mix and combine.

As seen in FIG. 1, debutanizer 100 is organized into different sections. For purposes of introducing the apparatus, there are three sections arranged vertically along height of the debutanizer 100. The top section 160 and bottom section 170 are above and below, respectively, the two vertical ends of the dividing wall 150. In between the top and bottom sections 160, 170 is the middle section 180. The dividing wall 150 bifurcates the middle section 180.

The top section of embodiment debutanizers is configured to fractionally distill across the entire diameter of the column. FIG. 1 shows the top section 160 of the debutanizer 100 as configured to rectify the middle cut product components from the top product components, namely residual propane from the introduced feed and butanes. Overhead product line 220 couples with overhead outlet 120, which is located above overhead liquid distributor 124. Overhead liquid distributor 124 is configured to spray a portion of the overhead product line 220 onto the topmost distillation tray 103 and is coupled to the overhead recycle line 222. Overhead recycle line 222 returns a portion of the condensed overhead product 220 to facilitate distillation in debutanizer 100. The remaining portion of the overhead product line 220 becomes C4s product stream 224. The distillation trays 104 fully extend across the diameter of the top section 160.

The bottom section of embodiment debutanizers is also configured to fractionally distill across the entire diameter of the column. FIG. 1 also shows the bottom section 170 of the debutanizer 100 as configured to strip the middle cut product components from the bottom product components, namely hexanes and heptanes, but also some normal pentanes. Bottoms product line 240 couples with bottoms outlet 140, which is located below bottoms sparger 144. Bottoms sparger 144 is configured to sparge a portion of the bottoms product line 240 below the bottommost distillation tray 105 and is coupled to the bottoms recycle line 242. Bottoms recycle line 242 returns a portion of the vaporized bottoms product line 240 to facilitate distillation in debutanizer 100. The remaining portion of the bottoms product line 240 becomes NG product stream 244. The distillation trays 104 fully extend across the diameter of the bottom section 170.

Although the middle section 180 is one physical section along the height of the column, similar to top section 160 and bottom section 170, the middle section 180 is different. Middle section contains two different distillation sections, which represent the beginning and a portion of the end of the fractionation process in embodiment debutanizers.

The feed section 192 is the one side of the bifurcated middle section 180 that receives the introduced feed. The upper portion of the feed section 192 is in direct fluid contact with the top section 160—it receives liquid from and passes vapor to the top section 160. The lower portion of the feed section 192 is in direct fluid contact with the bottom section 170—it receives vapor from and passes liquid to the bottom section 170.

The draw-off section 182 is the other side that passes the middle product components of the debutanizer 100. The upper portion of the draw-off section 182 is in direct fluid contact with the top section 160—it receives liquid from and passes vapor to the top section 160. The lower portion of the draw-off section 182 is in fluid contact with the bottom section 170—it receives vapor from and passes liquid to the bottom section 170.

Each of the four sections are at least in fluid communication with each other, although the feed section 192 is not in direct fluid communication with the draw-off section 182; rather, both sections 182, 192 are in fluid communication with each other around the dividing wall 150 through both the top and bottom sections 160, 170.

FIG. 1 shows the feed section 192 as a portion of the middle section 180 of the debutanizer 100. Feed section 192 is configured to receive the feed stream and to make the initial separation of the top product components from the bottom product components. Feed line 210 couples with side inlet 110, which couples with feed distributor 112. Feed distributor 112 includes feed vapor chimneys 114 for directing the vapor fraction from the introduced feed as well as allowing the vapor fraction passing up the feed section 192 from lower in the column to move further up the debutanizer 100. Feed distributor 112 also includes feed liquid distributors 116 for distributing the liquid fraction from the introduced feed as well as allowing the liquid fraction passing down the feed section 192 to proceed further down the debutanizer 100.

In some embodiments of the debutanizer, the feed section has two types of fractionation zones: a rectifying zone and a stripping zone. The two zones in the feed section of the embodiment debutanizers provide for the initial, bulk-type separation of the introduced feed stream. The rectifying zone 196 is the portion of the feed section 192 positioned above the side inlet 110 to the top of the dividing wall 150. The rectifying zone 196 is where the feed section 192 connects to the top section 160. Rectifying zone 196 directs the components of the feed stream that are bottom product components and some of the middle product components downward, permitting the top product components and some middle product components to rise higher than the topmost portion of the dividing wall 150 and enter the top section 160.

The stripping zone 194 is the portion of the feed section 192 positioned below the side inlet 110 to the bottom of the dividing wall 150. The stripping zone 194 is where the feed section 192 connects to the bottom section 170. Stripping zone 194 directs the components of the feed stream that are top product components upward, permitting the bottom product components and the middle product components to descend lower than the bottommost portion of the dividing wall 150 and enter the bottom section 170.

In some embodiments of the debutanizer, the physical volume of the rectifying zone is less than the physical volume of the stripping zone for the feed section.

In some other embodiments, the rectifying zone in the feed section is configured to process a greater amount of vapor flow than the stripping zone in the feed section. In some other embodiments, the rectifying zone in the feed section is configured to process a reduced amount of liquid flow than the stripping zone in the feed section.

FIG. 1 also shows the draw-off section 182. Draw-off section 182 is configured to receive the middle product components descending from the top section 160 and ascending from the bottom section 170. As well, the draw-off section 182 may separate the middle product components from both the top product components that may drift down from the top section 160 and the bottom product components that may rise up from the bottom section 170. Side product line 230 couples with side outlet 130, which couples with side product collector 132. Side product collector 132 includes draw-off vapor chimneys 134 for allowing the vapor fraction passing up the draw-off section 182 from lower in the column to move further up the debutanizer 100. Side product collector 132 also includes draw-off liquid distributors 136 for allowing the liquid fraction passing down the draw-off section 182 to proceed further down the debutanizer 100.

In some embodiments of the debutanizer, the draw-off section has two types of fractionation zones: a second rectifying zone and a second stripping zone. The two zones in the draw-off section of embodiment debutanizers provide for the final separation for the middle product components stream. The second rectifying zone 186 is the portion of the draw-off section 182 positioned below the side outlet 130 to the bottom of the dividing wall 150. The second rectifying zone 186 is where the draw-off section 182 connects to the bottom section 170. Second rectifying zone 186 directs the bottom product components downward, permitting the middle product components to rise to the side product collector 132.

The second stripping zone 184 is the portion of the draw-off section 182 positioned above the side outlet 130 to the top of the dividing wall 150. The second stripping zone 184 is where the draw-off section 182 connects to the top section 160. Second stripping zone 184 directs the top product components upward, permitting the middle product components to descend to the side product collector 132.

In some embodiments of the debutanizer, the physical volume of the rectifying zone is less than the physical volume of the stripping zone for the draw-off section.

In some other embodiments, the stripping zone in the draw-off section is configured to process a greater amount of vapor flow than the rectifying zone in the draw-off section. In some other embodiments, the rectifying zone in the draw-off section is configured to process a greater amount of liquid flow than the stripping zone in the draw-off section.

In some other embodiments of the debutanizer, the physical volume of the rectifying zone for the draw-off section is less than the physical volume of the rectifying zone of the feed section. In some other embodiments of the debutanizer, the physical volume of the stripping zone for the feed section is less than the physical volume of the stripping zone of the draw-off section. In some other embodiments of the debutanizer, the physical volume of the rectifying zone for the draw-off section is less than the physical volume of the stripping zone for the feed section. In some other embodiments of the debutanizer, the physical volume of the rectifying zone in the feed section is less than the physical volume of the stripping zone of the draw-off section.

In some other embodiments, the rectifier zone in the feed section is configured to process a greater amount of vapor and a reduced amount of liquid flows than the rectifier zone in the draw-off section. In some other embodiments, the stripper zone in the feed section is configured to process a greater amount of liquid and a reduced amount of vapor flows than the stripper zone in the draw-off section. In some other embodiments, the rectifier zone in the feed section is configured to process a greater amount of vapor and a reduced amount of liquid flows than the stripper zone in the draw-off section. In some other embodiments, the rectifier zone in the draw-off section is configured to process a greater amount of vapor and a reduced amount of liquid flows than the stripper zone in the feed section.

In some embodiments of the column, the position of the dividing wall may be entirely along a vertical centerline of the column. As seen in FIG. 1, the column centerline 101 (dot-dash arrow) is shown in portion to simplify the representation in FIG. 1. Column centerline 101 runs vertically through the entirety of the debutanizer 100. In some embodiments, the dividing wall 150 is positioned approximately on the vertical centerline 101 and runs substantially parallel with it, such as shown in FIG. 1. In such embodiments, both the feed section 192 and draw-off section 182 have about the same physical volume within the debutanizer 100.

Figure 2A:
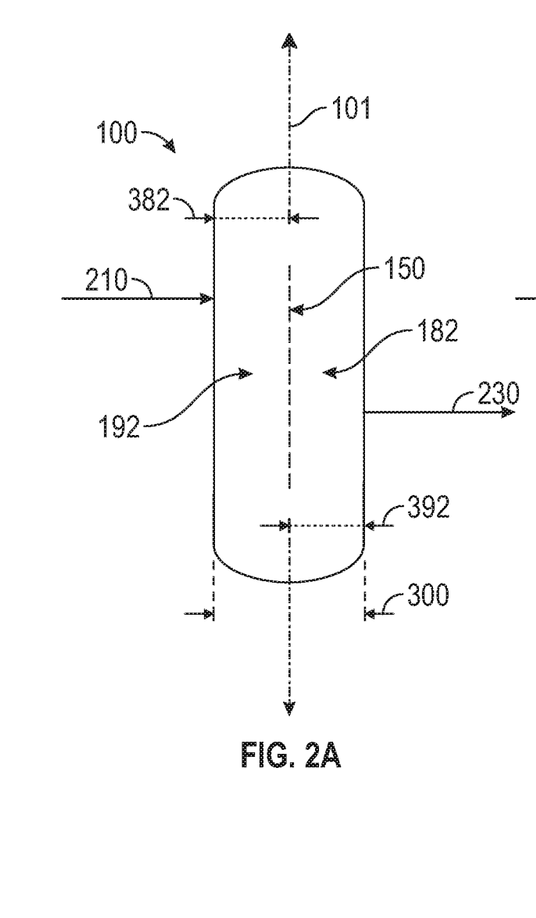
FIGS. 2A-C shows several generalized variations for configuration of the dividing wall within embodiment debutanizers.
Figure 2B:
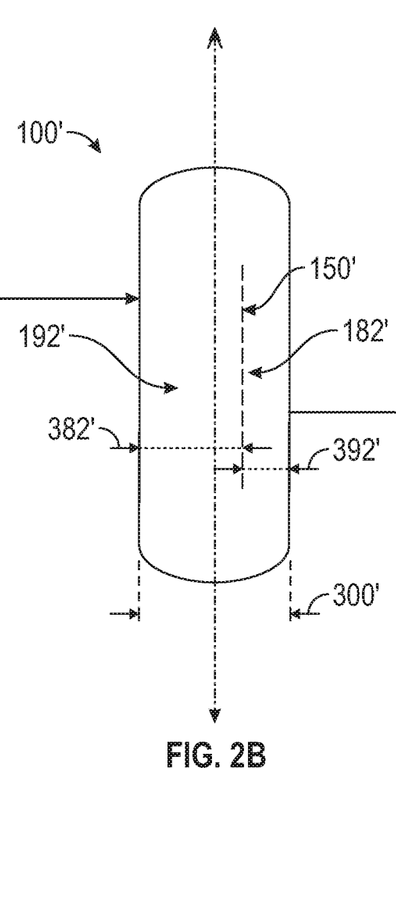
Figure 2C:
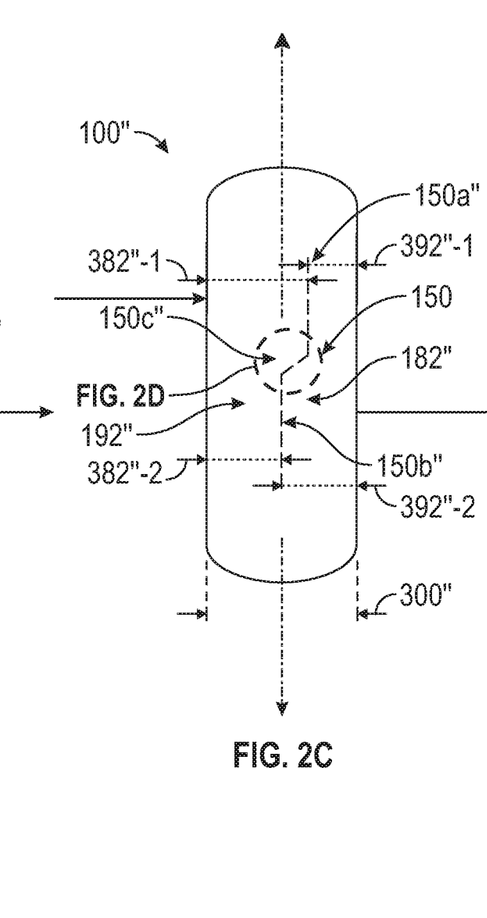

FIGS. 2A-C shows several generalized variations for configuration of the dividing wall within embodiment debutanizers. FIG. 2A is a generalize representation of embodiment debutanizer 100 as previously described. Dividing wall 150 is shown in relief as a dashed line. The vertical centerline 101 (dot-dash arrow) is shown in portion to simplify the representation in FIG. 2A. Feed line 210 and side product line 230 are shown; the other product lines are not shown again for simplicity. The dividing wall 150 is positioned approximately along the vertical centerline 101 such that the feed section 192 and the draw-off section 182 in the embodiment debutanizer have similar volumes.

Also shown for the first time in FIG. 2A is column diameter 300. Vertical centerline 101 bifurcates column diameter 300. Vertical centerline 101 and column diameter 300 are perpendicular to each other.

Also shown in FIG. 2A are two horizontal lengths associated with the column diameter 300: feed section width 392 (dotted line) and draw-off section width 382 (dotted line). Feed section width 392 and draw-off section width 382 represent the widths along the column diameter 300 of each of feed section 192 and draw-off section 182 between the column shell 102 and the dividing wall 150. As the sum of feed section width 392 and draw-off section width 382 is the column diameter 300, each may be expressed as a percentage of the column diameter 300. In the case of the embodiment column 100 as given in FIGS. 1 and 2A, feed section width 392 and draw-off section width 382 are approximately the same length; therefore, the length of each is approximately 50% of the column dimeter 300. Given that the vertical centerline 101 of the column 100 is half-way of the column diameter, the feed section width 392 and draw-off section width 382 may also be expressed as an off-set from the vertical centerline 101. In the case of the dividing wall 150 of FIGS. 1 and 2A, the offset would be about 0%.

Although the embodiment shown in FIGS. 1 and 2A is such that the dividing wall 150 is positioned approximately along the vertical centerline 101, embodiment debutanizers are not limited to such configurations. In some embodiments of the debutanizer, the dividing wall is configured such that it is substantially parallel with a vertical centerline and is not positioned along the vertical centerline, that is, the dividing wall is off-set from the vertical centerline. FIG. 2B shows a second embodiment debutanizer 100', where the entire dividing wall 150' (in relief) may be substantially parallel with the vertical centerline 101 but is not positioned approximately along the vertical centerline 101, that is, it is off-set. In the embodiment column 100' shown in FIG. 2B, the dividing wall 150' more positioned towards the draw-off product line 230 and away from the feed line 210. In such an embodiment, more column resources are dedicated to feed separation (feed section 192') than middle product separation (draw-off section 182'). Some flow and energy resources are dedicated to partitioning a middle product from the top and bottom sections in debutanizer 100'; however, such a configuration indicates that the volume of middle product is a minor product relative to the volumes of top and bottom products.

In some embodiments, the dividing wall is configured such that the dividing wall is completely off-set from but substantially parallel to the vertical centerline. In some configurations, the dividing wall is configured such that it is positioned closer to the side outlet than the side inlet. In such embodiments, feed section width 392' is greater than draw-off section width 382', such as shown in FIG. 2B. In some embodiments, the feed section width may be in a range of from about 55% to about 95% of the column diameter, such as 55%, 60%, 65%, 70%, 75%, 80%, 85%, 90%, or 95%.

In some other configurations, the dividing wall is configured such that it is positioned closer to the side inlet than the side outlet. In such embodiments, the draw-off section width is greater than the feed section width.

In such embodiments such as shown in FIG. 2B, the feed section has a volume that is greater than the draw-off section. In some such embodiments, the dividing wall is positioned such that the feed section 192' has a physical volume that is in a range of from about 10% to about 500% greater than the physical volume of the draw-off section 182' within embodiment column 150'.

Embodiment debutanizers may also use other configurations of dividing walls to customize relative volumes of products in the feed. For example, FIG. 2C introduces embodiment debutanizer 100". Debutanizer 100" is similar in external configuration as debutanizers 100 and 100'; however, the configuration of its dividing wall 150" splits the difference. In some embodiments of the debutanizer, the dividing wall is configured such that the dividing wall has an upper portion 150a", a middle portion 150c", and a lower portion 150b". In such embodiments, the upper portion 150a" may be configured such that it is substantially parallel with the vertical centerline 101 but is not positioned along the vertical centerline 101, whereas the lower portion 150b" is configured such that it is substantially parallel with and positioned along the vertical centerline 101. In such instances, middle portion 150c" is a transition between upper portion 150a" and lower portion 150b" of the dividing wall 150" and is not positioned or parallel with the vertical centerline 101. In such an embodiment column, the upper portion of the diving wall is off-set from the vertical centerline of the column, the lower portion of the diving wall is not off-set from the vertical centerline of the column, and the middle portion provides transition between the other two portions.

In examining this "S-type" configuration of dividing wall 150", it may be surmised that a greater proportion of top product is handled over the middle and bottoms product. The upper portion 150a" of the dividing wall 150", similar to the dividing wall 150', is configured such that it is substantially parallel with but is not positioned along the vertical centerline; rather, it is substantially parallel to the vertical centerline but is positioned closer to the draw-off product line 230. The lower portion 150b" of the dividing wall 150", similar to the dividing wall 150, is substantially parallel with and is positioned approximately along the vertical centerline. This may suggest that the relative volumes of the draw-off product and the bottoms product are similar to one another. Although other factors come into play, such as relative volatilities of the components and column internals, the relative component volume—that is, the sheer volume of one component over another—is a significant consideration.

The amount of off-set of the upper portion 150a" can be defined as it has been previously using the column diameter, a feed section width, and a draw-off section width, but as defined for the upper portion of the dividing wall. The column diameter 300" defines the total potential width of both upper feed section width 392"-1 and upper draw-off section width 382"-1. In some configurations, the upper portion of the dividing wall is configured such that the upper portion is positioned closer to the side outlet than the side inlet. In some embodiments, the dividing wall is configured such that upper feed section width 392"-1 is greater than upper draw-off section width 382"-1, such as shown in FIG. 2C. In some embodiments, the feed section width may be in a range of from about 55% to about 95% of the column diameter, such as 55%, 60%, 65%, 70%, 75%, 80%, 85%, 90%, or 95%.

In some other configurations, the upper portion of the dividing wall is configured such that the upper portion is positioned closer to the side inlet than the side outlet. In other such embodiments, the draw-off section width is greater than the feed section width.

In such embodiments, while the upper portion of the dividing wall is off-set, the bottom portion of the dividing wall is not off-set. Again, definitions can be structured for the lower portion of the dividing wall. In such embodiments, a lower feed section width 392"-2 and a lower draw-off section width 382"-2 are approximately the same.

Figure 2D:
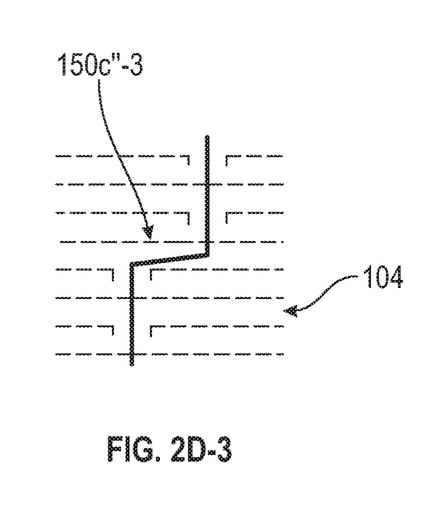
Figure 2D:
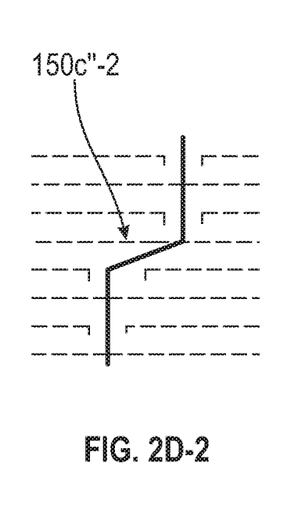
Figure 2D:
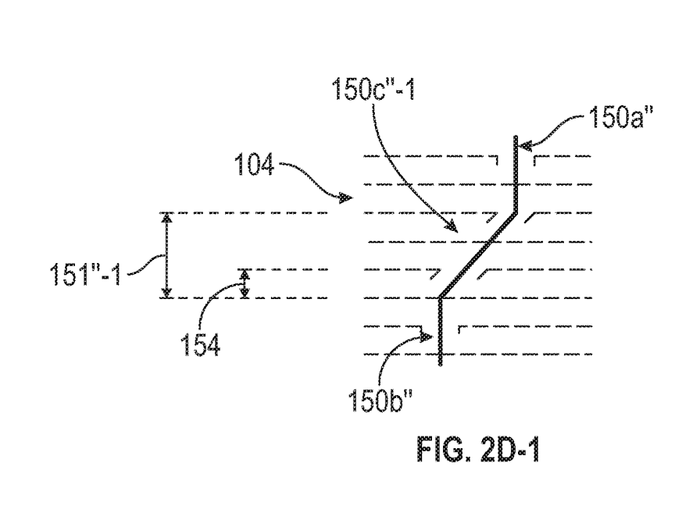

FIGS. 2D-1-3 is an inset showing several generalized variations for configuration of the middle portion of the dividing wall within embodiment debutanizers. The middle portion 150c" of the dividing wall 150" is a transition portion between lower portion 150b" and upper portion 150a". In embodiment debutanizers, several potential configuration options are feasible, as may be seen in inset FIGS. 2D-1-3.

In some embodiments, the middle portion of the dividing wall is configured to transition between the lower portion and the upper portion of the dividing wall in more than the vertical space of adjacent distillation trays. In FIG. 2D-1, the middle portion 150c"-1 is shown transitioning between lower portion 150b" and upper portion 150a" over the vertical spacing of several distillation trays 140 (in relief). The configuration of the distillation trays 140 also changes over the span of the vertical spacing so as to accommodate the middle portion 150c". In such embodiments, the vertical height 151"-1 of the middle portion 150c"-1 is greater than the vertical spacing 154 of adjacent distillation trays 104.

In some embodiments, the middle portion of the dividing wall is configured to transition between the lower portion and the upper portion of the dividing wall within the vertical space of adjacent distillation trays. In FIG. 2D-2, the middle portion 150c"-2 is shown transitioning between lower portion 150b" and upper portion 150a" over the vertical spacing of two adjacent distillation trays 140. In such embodiments, the vertical height (not shown) of the middle portion 150c"-2 is equal to the vertical spacing 154 of adjacent distillation trays 104.

In some embodiments, the middle portion of the dividing wall is configured to transition between the lower portion and the upper portion of the dividing wall in less than the vertical space of adjacent distillation trays. In FIG. 2D-3, the middle portion 150c"-3 is shown transitioning between lower portion 150b" and upper portion 150a" over the vertical spacing of between two distillation trays 140. In such embodiments, the vertical height (not shown) of the middle portion 150c"-3 is less than the vertical spacing 154 of adjacent distillation trays 104.

In some such embodiments, although not shown, the vertical height of the middle portion may be about 0. In such an instance, the middle portion is substantially parallel to the distillation trays and column diameter as well as substantially perpendicular to the vertical centerline of the embodiment debutanizer. In other embodiments, the start position, the end position, or both, of the middle portion is not limited to starting substantially at the location of a distillation tray, such as shown in FIG. 2D-3.

Along with the configuration of the middle portion, the vertical positon within the debutanizer of the middle portion relative to the side inlet and the side outlet provides for increasing or decreasing relative volumes of stripping and rectifying sections versus a purely vertical dividing wall. In some embodiments, the middle portion is positioned such that it is entirely above both the side inlet and the side outlet. In some embodiments, the middle portion is positioned such that part of it is above the side inlet, the rest is below the side inlet, and it is entirely above the side outlet. In such embodiments, the middle portion may be viewed as straddling the side inlet—positioned both above and below it at the same time. In some embodiments, the middle portion is positioned between the side inlet and the side outlet. In some embodiments, the middle portion is positioned such that it is entirely below the side inlet, part of it is above the side outlet and the rest is below the side outlet. As before, the middle portion may be viewed as straddling the side outlet—positioned both above and below it at the same time. In some embodiments, the middle portion is positioned such that it is entirely below both the side inlet and the side outlet.

In such embodiments such as shown in FIG. 2C, the feed section has a physical volume that is greater than the draw-off section. In some such embodiments, the dividing wall is configured such that the feed section has a physical volume that is in a range of from about 10% to about 500% greater than the physical volume of the draw-off section.

Internally, debutanizer features a plurality of distillation trays spread at regular vertical intervals from the bottom to the top of the column. Each distillation trays 104 encompass the area of the column where it is positioned such that fluid traversal upward (vapors) and downwards (liquids) are not only managed but also ensures intimate contact between each such that transport phenomenon occurs on the top surface of each tray at the conditions (pressure, temperature, flow) present and fluid bypass does not occur. In the top and bottom sections, each distillation tray and downcomer area, which is liquid filled during operation, encompasses the entire area within the column where positioned. In the middle section, the distillation trays cover the area of the feed section and the draw-off section, and effectively cover the same area but for the interruption by the dividing wall.

The debutanizer dividing wall column has a number of distillation trays to effect separation of components from the feeds stream into three product streams. The fractional distillation trays are operable at a given pressure and temperature differential between the bottom and the top of the column to separate the introduced C3-7 alkanes from each other into various product streams. Each tray promotes separation between the components in the liquid and the vapor state, whereas at each tray there is a given pressure and temperature state to foster transport. In some embodiments of the debutanizer, the column has a number of distillation trays in a range of from about 40 to about 60, or from about 45 to about 60, or from about 50 to about 55.

In some embodiments, the vertical span of the dividing wall is in a range of from about 20 to 30 distillation trays.

Each of the three sections—the top section, the middle section, and the bottom section—of the debutanizer has a number of distillation trays. In some embodiments, the top section has a number of distillation trays in a range of from 10 to 15. In some embodiments, the bottom section has a number of distillation trays in a range of from 10 to 15. In such embodiments, the middle section may have a number of distillation trays in a range of from 20 to 30.

In some embodiments, the bottom section and the top section of the debutanizer have the same number of trays. In such an embodiment, the dividing wall is configured such that its position is equidistant between the top section and the bottom section of the debutanizer. An example may include where the bottom portion of the dividing wall starts at tray number 12 and the top portion ends at tray number 31, with the same number of trays above and below the two ends of the dividing wall. Another example may include where the bottom portion of the dividing wall starts at tray number 15 and the top portion ends at tray number 39. In some other embodiments, the number of trays in the in the bottom section and the top section are not the same.

In some embodiments, the feed section and the draw-off section of the debutanizer have the same number of trays. That would mean that the vertical spacing between the distillation trays in both the feed section and the draw-off section would be the same. In some other embodiments, the feed section and the draw-off section do not have the same number of distillation trays. Various operational and compositional reasons may be present to have a different distillation tray count on the feed section versus the draw-off section that one of ordinary skill in distillation column design would recognize.

Due to the relative volatilities of the top product components, the middle product components, and the bottom product components, in embodiment debutanizers the side inlet is in a position further up the column in the feed section than the side outlet is in the draw-off section. FIG. 1 shows side inlet 110 in a relatively elevated position compared to side outlet 130. In some embodiments, the feed stream is introduced into the debutanizer at distillation tray number ranging from 25 to 30. In some embodiments, the C5s product stream is passed from the debutanizer at distillation tray number ranging from 15 to 20.

A feed stream is introduced into the column on the feed section of the dividing wall section of the column. The feed stream separates through repeated fractionation into at least three different product streams. One of these is removed from the draw-off section opposite the feed section. The other two product streams are removed near the top and bottom sections of the column similar to a conventional column configuration and operation.

The term "majority" means greater than 50.00% of the overall composition by the stated unit of measure (mass/volume/mole). The term "substantial" means greater than 10.00% but less than or equal to 50.00% (that is, not a majority) of the overall composition by the stated unit of measure (mass/volume/mole). The term "significant" means greater than 1.00% but less than or equal to 10.00% (that is, not substantial) of the overall composition by the stated unit of measure (mass/volume/mole). The term "detectable" means equal to or greater than 0.01% but less than or equal to 1.00% (that is, not significant) of the overall composition by the stated unit of measure (mass/volume/mole). The term "non-detectable" means less than 0.01% of the overall composition by the stated unit of measure (mass/volume/mole). However, "non-detectable" does not exclude the material from the composition; rather, the term indicates that, if determined to be present using industry-available analytical equipment its presence is de minimus for the purposes of this application.

The term "butanes" includes both iso-butane and normal butane. The term "pentanes" includes both iso-pentanes and normal pentanes. The term "hexanes" includes normal hexane. The term "heptanes" includes normal heptane.

An alkane C4+s stream is introduced into the feed section of the debutanizer. In some embodiments, the alkane C4+s stream has a majority amount of butanes and a substantial amount of pentanes. In some embodiments, the majority amount of butanes comprises a majority amount of normal butane and a substantial amount of iso-butane. In some embodiments, the majority amount of normal butane is in a range of from 50.0 mole % to about 60.0 mole %. In some embodiments, the substantial amount of iso-butane is in a range of from about 15.0 mole % to about 25.0 mole %. In some embodiments, the substantial amount of pentanes comprises a substantial amount of normal pentane and a substantial amount of iso-pentane. In some embodiments, the substantial amount of normal pentane is in a range of from 10.0 mole % to about 20.0 mole %. In some embodiments, the substantial amount of iso-pentane is in a range of from 10.0 mole % to about 20.0 mole %. In some embodiments, the alkane C4+s stream also has a detectable amount of propane. In some embodiments, the amount of propane is in a range of from about 0.1 mole % to about 1.0 mole %. In some embodiments, the alkane C4+s stream also has a significant amount of hexanes. In some embodiments, the amount of hexanes is in a range of from 1.0 mole % to about 5.0 mole %. In some embodiments, the alkane C4+s stream also has a significant amount of heptanes. In some embodiments, the amount of hexanes is in a range of from 1.0 mole % to about 5.0 mole %.

In some embodiments of the debutanizer, the vapor fraction by volume of the alkane C4+s stream is in a range of from about 0.3500 to less than 0.5000. Preheating the alkane C4+s stream such that a substantial volume of vapor is present in the introduced feed reduces the energy load on the debutanizer itself and facilitates near-immediate separation of the top product components in the feed section. In some other embodiments, the vapor fraction by volume is in a range of from about 0.4000 to about 0.4500.

An alkane C4s product stream comprises the top product components. The alkane C4s product stream is an overhead stream passing from top section of the debutanizer. In some embodiments, the C4s product stream has a majority amount of butanes. In some embodiments, the majority amount of butanes comprises a majority amount of normal butane and a substantial amount of iso-butane. In some embodiments, the majority amount of normal butane is in a range of from 65.0 mole % to about 75.0 mole %. In some embodiments, the substantial amount of iso-butane is in a range of from about 20.0 mole % to about 30.0 mole %. In some embodiments, the alkane C4s product stream also has a significant amount of propane. In some embodiments, the amount of propane is in a range of from 1.0 mole % to about 5.0 mole %. In some embodiments, the alkane C4s product stream also has a detectable amount of pentanes. In some embodiments, the detectable amount of pentanes comprises a detectable amount of normal pentane and a detectable amount of iso-pentane. In some embodiments, the detectable amount of normal pentane is in a range of from about 0.1 mole % to about 1.0 mole %. In some embodiments, the detectable amount of iso-pentane is in a range of from about 0.01 mole % to about 0.1 mole %. In some embodiments, the alkane C4s product stream has a non-detectable amount of hexanes. In some embodiments, the alkane C4s product stream has a non-detectable amount of heptanes.

An alkane C5s product stream comprises the middle product components. The alkane C5s product stream is a side draw stream passing from the draw-off section the debutanizer. In some embodiments, the alkane C5s product stream has a majority amount of pentanes. In some embodiments, the majority amount of pentanes comprises a substantial amount of iso-pentane and a substantial amount of normal pentane. In some embodiments, the substantial amount of iso-pentane is in a range of from about 35.0 mole % to about 45.0 mole %. In some embodiments, the substantial amount of normal pentane is in a range of from about 35.0 mole % to about 45.0 mole %. In some embodiments, the alkane C5s product stream has a significant amount of butanes. In some embodiments, the significant amount of butanes comprises a significant amount of normal butane and a detectable amount of iso-butane. In some embodiments, the significant amount of normal butane is in a range of from 1.0 mole % to about 5.0 mole %. In some embodiments, the detectable amount of iso-butane is in a range of from 0.01 mole % to about 0.1 mole %. In some embodiments, the alkane C5s product stream also has a detectable amount of hexanes. In some embodiments, the amount of hexanes is in a range of from about 0.1 mole % to 1.0 mole %. In some embodiments, the alkane C5s product stream also has a detectable amount of heptanes. In some embodiments, the amount of heptanes in a range of from 0.01 mole % to about 0.1 mole %. In some embodiments, the alkane C5s product stream has a non-detectable amount of propane.

A natural gasoline (NG) stream comprises the bottom product components. In some embodiments, the NG product stream has a majority amount of pentanes. In some embodiments, the majority amount of pentanes comprises a majority amount of iso-pentane and a substantial amount of normal pentane. In some embodiments, the majority amount of iso-pentane is in a range of from about 35.0 mole % to about 45.0 mole %. In some embodiments, the substantial amount of normal pentane is in a range of from 10.0 mole % to about 20.0 mole %. In some embodiments, the NG product stream also has a detectable amount of hexanes. In some embodiments, the amount of hexanes is in a range of from about 25.0 mole % to about 35.0 mole %. In some embodiments, the NG product stream also has a detectable amount of heptanes. In some embodiments, the amount of heptanes in a range of from 10.0 mole % to about 20.0 mole %. In some embodiments, the NG product stream has a non-detectable amount of propane. In some embodiments, the NG product stream has a non-detectable amount of butanes.

The volume of the product streams is in a ratio to the feed stream. On the basis of standard liquid volume flow, in some embodiments, the sum of the product streams passed from the debutanizer has a volume in a range of from about 100.0% to about 105.0% of the alkane C4+s stream introduced into the debutanizer. Standard liquid volume flow conditions are 60° F. and 14.696 psia (pounds per square inch absolute).

The volumes of the product streams are in a ratio to one another. Based on standard liquid volume flow, in some embodiments, the alkane C4 product stream passes from the debutanizer has a volume in a range of from about 65.0% to about 75.0% of the sum of the product streams from the debutanizer. Based on standard liquid volume flow, in some embodiments, the alkane C5s product stream passes from the debutanizer has a volume in a range of from about 10.0% to about 20.0% of the total volume of product streams from the debutanizer. Based on standard liquid volume flow, in some embodiments, the NG product stream passes from the debutanizer has a volume in a range of from about 10.0% to about 20.0% of the total volume of product streams from the debutanizer.

The Reid vapor pressure of the product streams are determined by ASTM D323-73/79 (ASTM International). In some embodiments, the alkane C5s product stream has a Reid vapor pressure in a range of from about 18.9 psia to about 19.3 psia. In some embodiments, the NG product stream has a Reid vapor pressure in a range of from about 11.0 psia and about 11.4 psia. In some other embodiments, the RVP of the NG product stream does is less than or equal to 13.0 psia. In some embodiments, the natural gasoline (NG) stream passing from the debutanizer requires no further adjustment in Reid vapor pressure (RVP) before gasoline blending.

Supporting equipment for embodiments of the apparatus may include additional standard components or equipment that enables and makes operable the described apparatuses, processes, methods, systems, and compositions of matter. Examples of such standard equipment known to one of ordinary skill in the art includes but are not limited to heat exchanges, pumps, blowers, reboilers, steam generation, condensate handling, membranes, single and multi-stage compressors, separation and fractionation equipment, valves, switches, controllers and pressure-, temperature-, level- and flow-sensing devices.

Operation, control and performance of portions of or entire steps of a process or method can occur through human interaction, pre-programmed computer control and response systems, or combinations thereof.

Method of Use

The debutanizer is configured to separate a C3-7 alkanes stream into three product streams, each mainly comprising butanes, pentanes, and natural gasoline. An embodiment process may include introducing an alkane C4+s stream into the debutanizer. Embodiment debutanizers configured as previously described, such as with a dividing wall such that there are four distillation sections—the top, the feed, the draw-off, and the bottom, are useful. The alkane C4+s stream as previously described for embodiment processes is introduced into the feed section of the debutanizer. As previously described, embodiment debutanizers may have a side inlet through with the alkane C4+s stream is introduced.

An embodiment process may also include operating the debutanizer. An embodiment process includes operating the debutanizer such that an alkane C4s product stream, an alkane C5s product stream, and a natural gasoline (NG) stream pass from the debutanizer. The debutanizer is operated such that an alkane C4s product stream passes from the top section, an alkane C5s product stream passes from the draw-off section, and a natural gasoline (NG) stream passes from the bottom section. Attributes of the various product streams produced by embodiment processes are as previously described.

In an embodiment of operating the debutanizer, the operable pressure range of the debutanizer may be in a range of from about 105 psia to about 140 psia, from about 110 pisa to about 135 psia, or from about 115 psia to about 130 psia. In an embodiment of operating the debutanizer, the pressure differential between the bottom of the column and the top of the column is in a range of from about 30 psid to about 35 psid, from about 25 psid to about 30 psid, from about 20 psid to about 25 psid, or from about 25 psid to about 30 psid.

In an embodiment of operating the debutanizer, the operable temperature range of the debutanizer may be in a range of from about 120° F. to about 300° F., to about 130° F. to about 290° F., to about 140° F. to about 280° F. In an embodiment of operating the debutanizer, the temperature differential between the bottom of the column and the top of the column is in a range of from about 100° F. difference to about 150° F. difference, to about 110° F. difference to about 140° F. difference, to about 120° F. difference to about 130° F. difference.

System

An embodiment natural gas liquids (NGL) system may utilize one or more of the embodiment debutanizers. An embodiment NGL system may receive raw or unrefined NGLs from the field or other processes for refining. A portion of such an embodiment system may be convert the introduced raw or unrefined NGLs into one or more alkane C4+s streams as previously described. The embodiment NGL systems may produce one or more alkane C4s product stream, alkane C5s product stream, and NG product stream.

Figure 3:
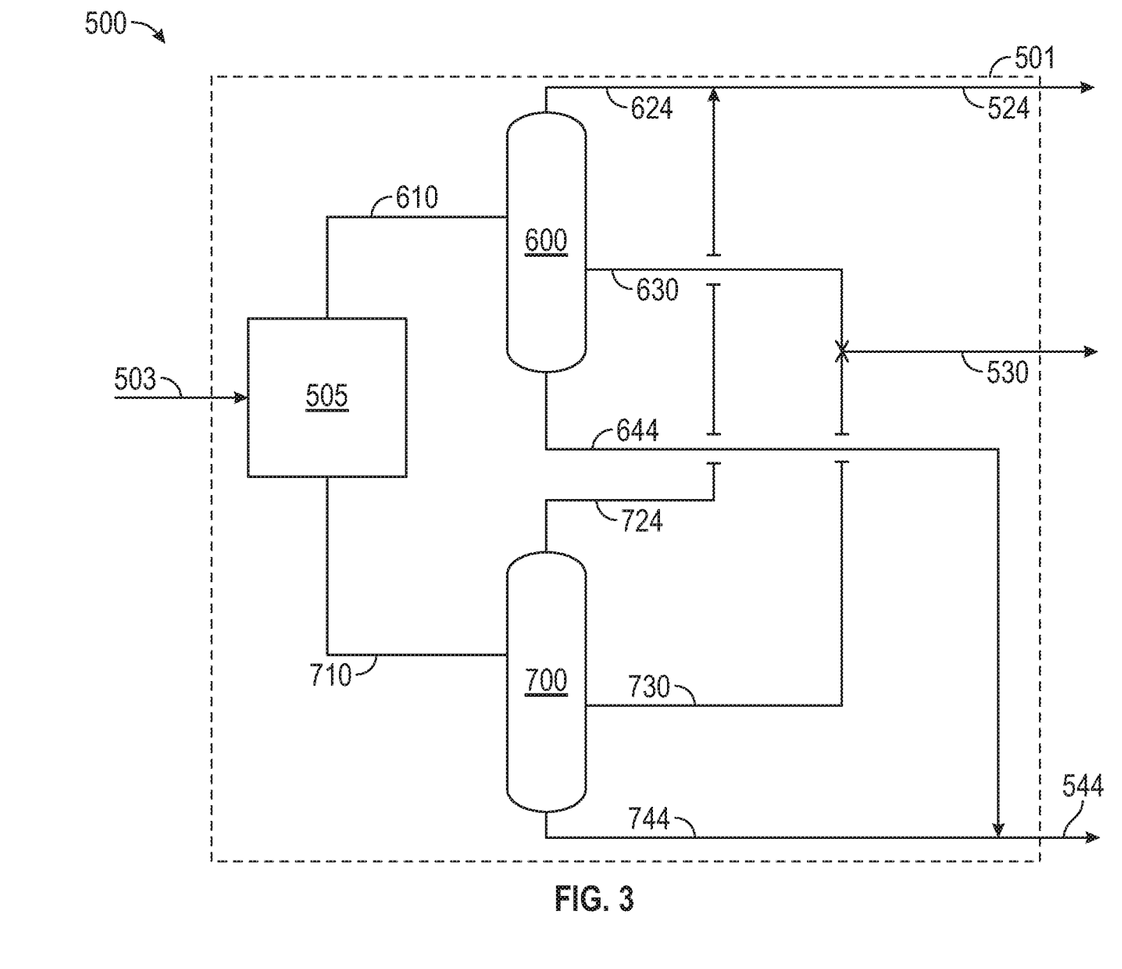
FIG. 3 shows a schematic of an embodiment system with parallel embodiment dividing wall debutanizer columns.

FIG. 3 shows a schematic of an embodiment system utilizing parallel embodiment debutanizers. Embodiment system 500 comprises a NGL refinery 501 (encompassing dot-dashed line). NGL refinery 501 includes NGL process train 505. NGL process train 505 couples to and is upstream of two embodiment debutanizers 600, 700. Raw or unrefined NGL 503 is introduced into NGL refinery 501 via NGL process train 505. From raw or unrefined NGL 503, NGL refinery 501 produces three product streams: combined C4s product stream 524, combined C5s product stream 530, and combined NG product stream 544.

NGL process train is a series of processing units, such as fractionation columns, pumps, absorbers, sulfur treatment, and compressors, many of which of ordinary skill in the treatment of natural gas liquids will recognize for partially converting an unrefined NGL into alkane C4+s streams for feeding the two debutanizers. NGL process train 505 is configured to convert the introduced unrefined NGL 503 into a first alkane C4+s stream 610 for the first debutanizer 600 and into a second alkane C4+s stream 710 for the second debutanizer 700. In some embodiments, the composition of first alkane C4+s stream and second alkane C4+s stream are about the same. In some embodiments, the volume of first alkane C4+s stream and second alkane C4+s stream are about the same. In some embodiments, the vapor fraction of first alkane C4+s stream and second alkane C4+s stream are about the same.

FIG. 3 shows the debutanizers 600, 700 are coupled parallel relative to one another via upstream NGL process train 505.

First debutanizer 600 as an embodiment debutanizer produces three products streams: first C4s product stream 624, first C5s product stream 630, and first NG product stream 644. Second debutanizer 700 as an embodiment debutanizer produces three products streams: second C4s product stream 724, second C5s product stream 730, and second NG product stream 744. In some embodiments, the composition of first C4s product stream and second C4s product stream are about the same. In some embodiments, the difference in the concentration of the butanes of the first C4s product stream and the concentration of the butanes of the second C4s product stream is in a range of from about 10% to about 20%. In some embodiments, the volume of first C4s product stream and second C4s product stream are about the same. In some other embodiments, the difference in the volume of the first C4s product stream and the second C4s product stream is in a range of from about 10% to about 20%. In some embodiments, the composition of first C5s product stream and second C5s product stream are about the same. In some embodiments, the difference in the concentration of the pentanes of the first C5s product stream and the concentration of the pentanes of the second C5s product stream is in a range of from about 10% to about 20%. In some embodiments, the volume of first C5s product stream and second C5s product stream are about the same. In some other embodiments, the difference in the volume of the first C5s product stream and the second C5s product stream is in a range of from about 10% to about 20%. In some embodiments, the composition of first NG product stream and second NG product stream are about the same. In some embodiments, the difference in the concentration of the hexanes of the first NG product stream and the concentration of the hexanes of the second NG product stream is in a range of from about 10% to about 20%. In some embodiments, the volume of first NG product stream and second NG product stream are about the same. In some other embodiments, the difference in the volume of the first NG product stream and the second NG product stream is in a range of from about 10% to about 20%.

Both debutanizers 600, 700 are also coupled parallel to one another via the three downstream product streams of NGL refinery 501. First C4s product stream 624 and second C4s product stream 724 combine to form combined C4s product stream 524; First C5s product stream 630 and second C5s product stream 730 combine to form combined C5s product stream 530; and first NG product stream 644 and second NG product stream 744 combine to form combined NG product stream 544. The volume of the product streams are in a ratio to one another. Based on standard liquid volume flow, in some embodiments, the combined C4s product stream passes from the NGL refinery has a volume in a range of from about 65.0% to about 75.0% of the sum of the product streams from the NGL refinery. Based on standard liquid volume flow, in some embodiments, the combined C5s product stream passes from the NGL refinery has a volume in a range of from about 10.0% to about 20.0% of the total volume of product streams from the NGL refinery. Based on standard liquid volume flow, in some embodiments, the combined NG product stream passes from the NGL refinery has a volume in a range of from about 10.0% to about 20.0% of the total volume of product streams from the NGL refinery.

The combined C4s product stream 524 comprises the top product components from the system debutanizers. In some embodiments, the combined C4s product stream has a majority amount of butanes. In some embodiments, the majority amount of butanes comprises a majority amount of normal butane and a substantial amount of iso-butane. In some embodiments, the majority amount of normal butane is in a range of from 65.0 mole % to about 75.0 mole %. In some embodiments, the substantial amount of iso-butane is in a range of from about 20.0 mole % to about 30.0 mole %. In some embodiments, the combined C4s product stream also has a significant amount of propane. In some embodiments, the amount of propane is in a range of from 1.0 mole % to about 5.0 mole %. In some embodiments, the combined C4s product stream also has a detectable amount of pentanes. In some embodiments, the detectable amount of pentanes comprises a detectable amount of normal pentane and a detectable amount of iso-pentane. In some embodiments, the detectable amount of normal pentane is in a range of from about 0.1 mole % to about 1.0 mole %. In some embodiments, the detectable amount of iso-pentane is in a range of from about 0.01 mole % to about 0.1 mole %. In some embodiments, the combined C4s product stream has a non-detectable amount of hexanes. In some embodiments, the combined C4s product stream has a non-detectable amount of heptanes.

The combined C5s product stream 530 comprises the middle product components from the two system debutanizers. In some embodiments, the combined C5s product stream has a majority amount of pentanes. In some embodiments, the majority amount of pentanes comprises a substantial amount of iso-pentane butane and a substantial amount of normal pentane. In some embodiments, the substantial amount of iso-pentane is in a range of from about 35.0 mole % to about 45.0 mole %. In some embodiments, the substantial amount of normal pentane is in a range of from about 35.0 mole % to about 45.0 mole %. In some embodiments, the combined C5s product stream has a significant amount of butanes. In some embodiments, the significant amount of butanes comprises a significant amount of normal butane and a detectable amount of iso-butane. In some embodiments, the significant amount of normal butane is in a range of from 1.0 mole % to about 5.0 mole %. In some embodiments, the detectable amount of iso-butane is in a range of from 0.01 mole % to about 0.1 mole %. In some embodiments, the combined C5s product stream also has a detectable amount of hexanes. In some embodiments, the amount of hexanes is in a range of from about 0.1 mole % to 1.0 mole %. In some embodiments, the combined C5s product stream also has a detectable amount of heptanes. In some embodiments, the amount of heptanes in a range of from 0.01 mole % to about 0.1 mole %. In some embodiments, the combined C5s product stream has a non-detectable amount of propane.

The combined natural gasoline (NG) product stream 544 comprises the bottom product components from the two system debutanizers. In some embodiments, the combined NG product stream has a majority amount of pentanes. In some embodiments, the majority amount of pentanes comprises a majority amount of iso-pentane and a substantial amount of normal pentane. In some embodiments, the majority amount of iso-pentane is in a range of from about 35.0 mole % to about 45.0 mole %. In some embodiments, the substantial amount of normal pentane is in a range of from 10.0 mole % to about 20.0 mole %. In some embodiments, the combined NG product stream also has a detectable amount of hexanes. In some embodiments, the amount of hexanes is in a range of from about 25.0 mole % to about 35.0 mole %. In some embodiments, the combined NG product stream also has a detectable amount of heptanes. In some embodiments, the amount of heptanes in a range of from 10.0 mole % to about 20.0 mole %. In some embodiments, the combined NG product stream has a non-detectable amount of propane. In some embodiments, the combined NG product stream has a non-detectable amount of butanes.

In some embodiments, the combined C5s product stream has a Reid vapor pressure in a range of from about 18.9 psia and about 19.3 psia. In some embodiments, the combined NG product stream has a Reid vapor pressure in a range of from about 11.0 psia and about 11.4 psia. In some embodiments, the combined NG product stream passing from the debutanizer requires no further adjustment in Reid vapor pressure (RVP) before gasoline blending.

Method of Use

The NGL refinery is configured to separate a raw or unrefined NGL stream at least in part into three product streams, each mainly comprising butanes, pentanes, and natural gasoline. An embodiment process may include introducing an unrefined NGL stream into a NGL refinery. Embodiment debutanizers configured as previously described, such as with a dividing wall such that there are four distillation sections—the top, the feed, the draw-off, and the bottom, are useful. Embodiment processes may include where the NGL refinery has a first embodiment debutanizer and a second embodiment debutanizer coupled in parallel relative to each other.

The NGL refinery produces the feedstock that the parallel debutanizers use to make the combined products that pass the NGL refinery. An embodiment process may include where the NGL refinery 501, though the NGL process train 503, converts a portion of the unrefined NGL stream 503 into two alkane C4+s streams: a first alkane C4+s stream 610 and a second alkane C4+s stream 710. Each stream is introduced into the first and second debutanizers 600, 700, respectively. As previously described, the volumes, the compositions, the vapor fractions, any or all may be the same.

An embodiment process may also include operating each of the debutanizers individually. An embodiment process includes operating each debutanizer such that an alkane C4s product stream, an alkane C5s product stream, and a natural gasoline (NG) stream each pass from each of the parallel debutanizers. The debutanizer are operated similarly as previously described, with an alkane C4s product stream passing from the top section, an alkane C5s product stream passing from the draw-off section, and a natural gasoline (NG) stream passing from an the bottom section. The attributes of each product streams produced by the embodiment processes are as previously described.

In some instances, the NGL refinery produces single product streams. In some embodiment, the NGL refinery is operated such that the first C4s product stream and the second C4s product stream form a combined C4s product stream. As well, the NGL refinery is operated such that the first C5s product stream and the second C5s product stream form a combined C4s product stream. Additionally, the NGL refinery is operated such that the first NG product stream and the second NG product stream form a combined NG product stream. The three combined streams are separately passed from the NGL refinery as final products. In some such embodiments, the combined NG product stream requires no further adjustment to Reid vapor pressure before gasoline blending.

Unless defined otherwise, all technical and scientific terms used have the same meaning as commonly understood by one of ordinary skill in the art to which these systems, apparatuses, methods, processes and compositions belong.

The singular forms "a," "an," and "the" include plural referents, unless the context clearly dictates otherwise.

As used here and in the appended claims, the words "comprise," "has," and "include" and all grammatical variations thereof are each intended to have an open, non-limiting meaning that does not exclude additional elements or steps.

"Optionally" means that the subsequently described event or circumstances may or may not occur. The description includes instances where the event or circumstance occurs and instances where it does not occur.

The term "substantially" as used refers to a majority of, or mostly, as in at least about 50%, 60%, 70%, 80%, 90%, 95%, 96%, 97%, 98%, 99%, 99.5%, 99.9%, 99.99%, or at least about 99.999% or more.

When the word "approximately" or "about" are used, this term may mean that there can be a variance in value of up to ±10%, of up to 5%, of up to 2%, of up to 1%, of up to 0.5%, of up to 0.1%, or up to 0.01%.

Ranges may be expressed as from about one particular value to about another particular value, inclusive. When such a range is expressed, it is to be understood that another embodiment is from the one particular value to the other particular value, along with all particular values and combinations thereof within the range.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed is:

1. A process, comprising:
   introducing an alkane C4+s stream into a feed section of a debutanizer with a dividing wall,
   where the debutanizer has a feed section, a top section, a bottom section, and a draw-off section; and
   operating the debutanizer with a dividing wall such that an alkane C4s product stream passes from a top section, an alkane C5s product stream passes from the draw-off section, and a natural gasoline (NG) product stream passes from the bottom section, where the NG product stream requires no further adjustment to Reid vapor pressure (RVP) before gasoline blending.

2. The process of claim 1 where the alkane C4+s stream comprises a majority amount of butanes and a substantial amount of pentanes.

3. The process of claim 2 where the majority amount of butanes comprises a majority amount of normal butane and a substantial amount of iso-butane, and where the substantial amount of pentanes comprises a substantial amount of normal pentane and a substantial amount of isopentane.

4. The process of claim 1 where the alkane C4s product stream comprises a majority amount of butanes.

5. The process of claim 4 where the majority amount of butanes comprises a majority amount of normal butane and a substantial amount of iso-butane.

6. The process of claim 1 where the alkane C5s product stream has a majority amount of pentanes.

7. The process of claim 6 where the majority amount of pentanes comprises a substantial amount of iso-pentane and a substantial amount of normal pentane.

8. The process of claim 1 where the natural gasoline (NG) product stream has a majority amount of pentanes and has a Reid vapor pressure value in a range of from about 18.9 to about 19.3 pounds-per-square-inch absolute (psia).

9. The process of claim 8 where the majority amount of pentanes comprises a majority amount of iso-pentane and a substantial amount of normal pentane.

* * * * *

UNITED STATES PATENT AND TRADEMARK OFFICE
CERTIFICATE OF CORRECTION

PATENT NO. : 11,338,219 B2
APPLICATION NO. : 16/992661
DATED : May 24, 2022
INVENTOR(S) : Hae Yong Noh It is certified that error appears in the above-identified patent and that said Letters Patent is hereby corrected as shown below:

In the Claims

In Claim 8, Column 20, Line 21, please replace "18.9" with --11.0--.
In Claim 8, Column 20, Line 22, please replace "19.3" with --11.4--.

Signed and Sealed this
Sixteenth Day of August, 2022

Katherine Kelly Vidal
*Director of the United States Patent and Trademark Office*